United States Patent [19]

Meyers et al.

[11] Patent Number: 5,320,955
[45] Date of Patent: Jun. 14, 1994

[54] 10'-DESMETHOXYSTREPTONIGRIN PRODUCTION BY STREPTOMYCES ALBUS

[75] Inventors: Edward Meyers, East Brunswick, N.J.; Terrence W. Doyle, Killingworth, Conn.; Veeraswamy Manne, Yardley, Pa.; Wen-Chih Liu, Princeton Junction, N.J.

[73] Assignee: E. R. Squibb & Sons, Inc., Princeton, N.J.

[21] Appl. No.: 922,260

[22] Filed: Jul. 30, 1992

Related U.S. Application Data

[62] Division of Ser. No. 705,481, May 24, 1991, Pat. No. 5,158,960.

[51] Int. Cl.$^5$ .................. C12P 17/12; C12N 1/20
[52] U.S. Cl. ............................ 435/122; 435/253.5; 435/887
[58] Field of Search ................ 435/188, 122, 253.5, 435/887

[56] References Cited

U.S. PATENT DOCUMENTS

| | | | |
|---|---|---|---|
| 3,372,090 | 3/1968 | Marsh et al. | 424/114 |
| 4,789,673 | 12/1988 | Donatsch et al. | 514/214 |

FOREIGN PATENT DOCUMENTS

| | | |
|---|---|---|
| 61-280490 | 12/1986 | Japan. |
| 64-13083 | 1/1989 | Japan. |
| 3083980 | 4/1991 | Japan. |
| 1043858 | 9/1966 | United Kingdom. |

OTHER PUBLICATIONS

Gould et al., Streptonigrin; *Fort Schritteder Chem. Org. Natur.*, Springer Verlag, Vienna, NY, pp. 77-114 (1982).

Isshiki et al., A New Antitumor Antibiotic: Demethylstreptonigrin; *The Journal of Antibiotics*, vol. XXXIX, No. 7, pp. 1013-1015 (1986).

Inouye et al., Biological Properties of Streptonigrin Derivatives; *The Journal of Antibiotics*, vol. XXXVIII, No. 10, pp. 1429-1432 (1985).

Take et al., Biological Properties of Streptonigrin Derivatives; *The Journal of Antibiotics*, vol. XLII, No. 6, pp. 968-976 (1989).

Inouye et al., Effects of Streptonigrin Derivatives and Sakyomicin A on the Respiration of Isolated Rat Liver Mitochondria; *The Journal of Antibiotics*, vol. XXXIX, No. 4, pp. 550-556 (1986).

Kozlova et al., Streptonigrone, a minor component of the bruneomycin complex; *Antibiot. Khimioter.*, 35(5) (1990) (abstract only).

Balitz et al., Isolation of Lavendamycin A New Antibiotic From *Streptomyces Lavendulae*; *The Journal of Antibiotics*, vol. 35, No. 3, pp. 259-265 (1982).

Doyle et al., Structure Determination of Lavendamycin-A New Antitumor Antibiotic from Streptomyces Lavendulae; *Tetrahedron Letters*, 22, p. 4595 (1981).

Okada et al., Biological Properties of Streptonigrin Derivatives II. Inhibition of Reverse Transcriptase Activity; *The Journal of Antibiotics*, vol. XXXIX, No. 2, pp. 306-308 (1986).

Shaikh et al., Streptonigrin. 1. Structure-Activity Relationships among Simple Bicyclic Analogues. Rate Dependence of DNA Degradation on Quinone Reduction Potential; *J. Med. Chem.*, 29, pp. 1329-1340 (1986).

Mizuno, Comparative Effects of Streptonigrin Derivatives on Tissue Culture Cells; *Biochemical Pharmacology*, vol. 16, pp. 933-940 (1967).

*Primary Examiner*—Douglas W. Robinson
*Assistant Examiner*—S. Saucier
*Attorney, Agent, or Firm*—Suzanne E. Babajko

[57] ABSTRACT

10'-Desmethoxystreptonigrin, obtainable by cultivation of a strain of *Streptomyces albus*, A.T.C.C. No. 55161, and salts, esters and amides thereof. The novel compounds have antitumor and antibiotic activity.

4 Claims, No Drawings

10'-DESMETHOXYSTREPTONIGRIN PRODUCTION BY *STREPTOMYCES ALBUS*

This is a division of application Ser. No. 07/705,481, filed May 24, 1991, now U.S. Pat. No. 5,158,960.

FIELD OF THE INVENTION

The instant invention relates to a novel antitumor antibiotic which may be obtained by cultivation of a strain of *Streptomyces albus*, to salts, esters and amides thereof, and to compositions containing and methods of using the inventive compounds. The instant invention also relates to the novel strain of *Streptomyces albus*.

BACKGROUND OF THE INVENTION

Streptonigrin, 5'-amino-6'-(7-amino-5,-8-dihydro-6-methoxy-5,8-dioxo-2-quinolyl)-4'-(8'-hydroxy-9',10'-dimethoxyphenyl)-3'-methyl-2'-pyridinecarboxylic acid, having the structure:

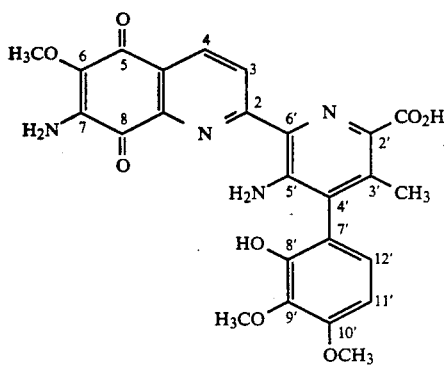

has previously been obtained from the microorganism *Streptomyces flocculus*. While streptonigrin has shown activity as an antitumor antibiotic, this compound also exerts a significant toxic effect, for example, in bone marrow depression. The art has thus continued to seek less toxic, as well as more potent, antitumor antibiotic agents.

SUMMARY OF THE INVENTION

Cultivation of a strain of the microorganism *Streptomyces albus*, which has been deposited in the American Type Culture Collection with the accession number, A.T.C.C. 55161, yields the novel substance hereinafter referred to as "10'-desmethoxystreptonigrin". This novel substance has been found to have antibiotic activity, particularly broad-spectrum antibacterial activity, and has also been found to possess antitumor activity, particularly against human tumor cells. In view of the ability of the compound to inhibit farnesylation of ras oncogene p21 protein, it is expected that the inventive compound may be employed in preventing, as well as treating, tumors. Salts, esters and amides of, and compositions containing, the novel substance are also provided by the instant invention.

10'-Desmethoxystreptonigrin has been analyzed and has been found to have the general chemical structure:

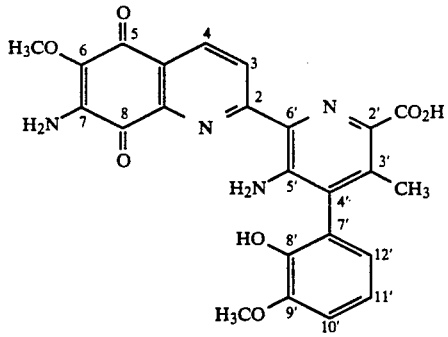

corresponding to the chemical name 5'-amino-6'-(7-amino-5,8-dihydro-6-methoxy-5,8-dioxo-2-quinolyl)-4'-(8'-hydroxy-9'-methoxyphenyl)-3'-methyl-2'-pyridinecarboxylic acid.

The instant invention also relates to the novel strain of *Streptomyces albus* described herein.

DESCRIPTION OF THE PREFERRED EMBODIMENTS

The Microorganism

The organism which may be used to produce 10'-desmethoxystreptonigrin, *Streptomyces albus*, has been isolated from soil, in particular, from soil obtained in Yosemite National Park, Calif. A subculture of the microorganism may be obtained from the permanent collection of the American Type Culture Collection, 12301 Parklawn Drive, Rockville, Md. 20852, where it was deposited on Mar. 14, 1991 and received the number A.T.C.C. 55161. In addition to the specific microorganism described herein, it should be understood that mutants, such as those produced by the use of chemical or physical mutagens including X-rays, etc., and organisms whose genetic makeup has been modified by molecular biology techniques, may also be cultivated to produce 10'-desmethoxystreptonigrin.

*Streptomyces albus* A.T.C.C. No. 55161 may be isolated from the soil in which it is present by first suspending the soil sample in a sterile diluent such as buffered saline containing 0.01% gelatin, and shaking vigorously. A dilution of this suspension may then be plated onto a nutrient medium that has been supplemented with cycloheximide. The composition of an exemplary such medium is:

| | |
|---|---|
| Glycerol | 12.5 g |
| Arginine | 1.0 g |
| NaCl | 20.0 g |
| $K_2HPO_4$ | 1.0 g |
| $MgSO_4.7H_2O$ | 0.5 g |
| $Fe_2(SO_4).6H_2O$ | 0.01 g |
| $CuSO_4.5H_2O$ | 0.001 g |
| $ZnSO_4.7H_2O$ | 0.001 g |
| $MnSO_4.H_2O$ | 0.008 g |
| Agar | 15 g |
| Distilled water | 1000 mL |
| Cycloheximide* | 10 ml of a 1% aqueous solution |

*Filter sterilized and added to the remainder of the medium, which is adjusted to a pH of about 7 and sterilized by autoclaving at 121° C. for 30 minutes prior to addition of the cycloheximide.

After 5 to 8 days incubation at room temperature, the colonies of *Streptomyces albus* may be isolated from the plated soil sample and transferred to slants of tomato paste-oatmeal agar. This medium may be prepared by adding one volume of water containing tomato paste (4%) and oatmeal (4%) to one volume of boiling water containing 3% agar.

Cultures of *Streptomyces albus* A.T.C.C. No. 55161 that have been grown on Inorganic Salts-Starch Agar (ISP medium 4) for two weeks show oyster white (ISCC-NBS white (263)) aerial mycelium and smooth, spiral spore chains. The presence of spores in chains serves to identify the organism as a member of the genus Streptomyces. Substrate mycelium is cream colored to brown (Prauser color code Coo5 m). No spore formation is observed when the organism is grown on ISP medium 2 or ISP medium 6. On ISP medium 2, a soluble, faint rose-colored pigment is produced. No melanoid pigments are produced on ISP medium 6 or ISP medium 7.

The following carbon sources can be utilized for growth when incorporated in ISP medium 9 as the sole carbon source: glucose, mannitol, xylose, rhamnose, fructose, raffinose and salicin. On the other hand, arabinose, sucrose and inositol do not support growth under similar conditions. Readings were made after 7 and 14 days incubation at 28° C.

These characteristics serve to identify the organism as a strain of *Streptomyces albus*, in accordance with the description given in Nonomura, "Key for classification and identification of 458 species of the streptomycetes, included in ISP." J. Ferment. Technol. 52: 78–92 (1974).

The instant invention provides the novel strain of *Streptomyces albus* designated by A.T.C.C. No. 55161. This organism is preferably isolated from soil, such as by the cultivation and isolation methods described herein. Also provided are organisms which have the identifying characteristics of the strain designated by A.T.C.C. No. 55161 as discussed above, and which are capable of producing 10'-desmethoxystreptonigrin. Such organisms include those originally designated as *Streptomyces albus* A.T.C.C. No. 55161 which have been modified by physical, chemical, or biological means. Biologically pure cultures of the organisms described herein are preferred.

The Antibiotic

10'-Desmethoxystreptonigrin for use as an antibiotic may be produced by cultivating *Streptomyces albus* A.T.C.C. No. 55161 at, or about, room temperature (25° C.) under submerged aerobic conditions in an aqueous nutrient medium containing assimilable sources of carbon and nitrogen. The fermentation is carried out until substantial antibiotic activity is imparted to the medium, usually about 96 to 144 hours. The fermentation, as well as subsequent isolation steps, may be monitored by means of a conventional paper discagar diffusion assay with *Staphylococcus aureus* as the assay organism. 10'-Desmethoxystreptonigrin may be isolated and purified by art-recognized techniques from the broth supernatant after removal of the cell mass by centrifugation.

To obtain the antibiotic from the fermentation supernatant, the antibiotic may be extracted into ethyl acetate from the acidified (pH 3) supernatant. The organic layer may then be extracted with 5% aqueous sodium carbonate, resulting in the transfer of the antibiotic into the aqueous layer. After careful acidification of the aqueous layer to a pH of about 3, the antibiotic may be re-extracted into ethyl acetate. The ethyl acetate layer may then be concentrated in vacuo to yield a residue which, after dissolving in a minimal amount of methanol, may be charged onto a DEAE (diethylaminoethyl) cellulose column packed in methanol. After washing the column with methanol to remove inactive impurities, the column may be developed with 1% acetic acid in methanol. Fractions may be collected, and the active fractions combined and concentrated to dryness. The residue may then be crystallized and recrystallized from acetone, to yield blackish-red needles of pure 10'-desmethoxystreptonigrin. 10'-Desmethoxystreptonigrin for use as an antitumor agent, or for other uses, may be similarly obtained.

Thus, the instant invention provides 10'-desmethoxystreptonigrin produced by a microorganism capable of producing 10'-desmethoxystreptonigrin, preferably *Streptomyces albus* A.T.C.C. No. 55161 or a strain of *Streptomyces albus* having the identifying characteristics of the strain designated by A.T.C.C. No. 55161, wherein the 10'-desmethoxystreptonigrin is at least partially isolated from the medium containing the organism, or a salt, ester or amide thereof.

10'-Desmethoxystreptonigrin, a blackish-red substance, has been found to have the following characteristics:

(1) Accurate mass measurement of the $M+H^+$ ion in the Fast Atom Bombardment Mass Spectrum (FAB-MS) yielded a value of 476.1406. The value calculated for the formula $C_{24}H_{20}N_4O_7$ is 476.1410;

(2) The UV spectrum of 10'-desmethoxystreptonigrin, recorded in methanol, showed two distinct peaks, with absorption maxima (molar extinction coefficient) values of 247 nm (34,800) and 379 nm (14,900). The corresponding values in acidified methanol were 247 nm (41,600) and 379 nm (17,400). In alkaline methanol, the corresponding values were 246 nm (43,600) and 380 nm (16,100);

(3) Absorption maxima of the infrared spectrum of 10'-desmethoxystreptonigrin recorded in KBr are set forth in the following Chart 1;

(4) The $^{13}C$ and $^1H$ NMR spectra of 10'-desmethoxystreptonigrin are set forth in the following Chart 2; and (5) The electrophoretic mobility of 10'-desmethoxystreptonigrin on paper relative to vitamin $B_{12}$ (0.0) and p-nitrobenzenesulfonate anion (1.0) when using a buffer consisting of 0.05M sodium carbonate and 0.05M sodium bicarbonate balanced to pH 9.2 is 0.34; is 0.38 when using a buffer composed of 0.05M $KH_2PO_4$ and 0.05M $K_2HPO_4$ balanced to pH 7.0; and is 0.08 with a buffer of 0.05M $KH_2PO_4$ balanced to pH 4.5.

Chart 1
IR Absorption Maxima in KBr of
10'-Desmethoxystreptonigrin

| max (cm$^{-1}$) | Relative Intensity | max (cm$^{-1}$) | Relative Intensity |
|---|---|---|---|
| 3388 | 39.8 | 1234 | 37.7 |
| 3372 | 40.5 | 1214 | 47.3 |
| 3356 | 39.9 | 1184 | 65.7 |
| 3272 | 42.8 | 1166 | 63.4 |
| 3010 | 70.2 | 1096 | 65.5 |
| 2942 | 68.3 | 1074 | 56.6 |
| 2840 | 73.4 | 1038 | 62.1 |
| 1738 | 32.2 | 1008 | 63.0 |
| 1684 | 59.2 | 920 | 79.8 |
| 1632 | 53.7 | 876 | 84.5 |
| 1602 | 19.0 | 830 | 85.8 |
| 1586 | 22.4 | 808 | 86.5 |
| 1564 | 41.3 | 790 | 81.3 |
| 1546 | 49.6 | 746 | 63.8 |
| 1480 | 55.2 | 712 | 78.5 |
| 1442 | 55.2 | 686 | 84.3 |

Chart 1
IR Absorption Maxima in KBr of
10'-Desmethoxystreptonigrin

| max (cm$^{-1}$) | Relative Intensity | max (cm$^{-1}$) | Relative Intensity |
|---|---|---|---|
| 1400 | 57.3 | 658 | 84.7 |
| 1376 | 64.6 | 582 | 79.5 |
| 1344 | 29.0 | 556 | 85.7 |
| 1276 | 57.4 | 522 | 85.5 |

Chart 2
NMR data of 10'-Desmethoxystreptonigrin (in DMSO$^+$)

| C position | δC (ppm) | δH (ppm) | C—H long-range coupling (Hz) |
|---|---|---|---|
| C-2 | 159.88 | | 8.35 (7.5 Hz) |
| C-3 | 126.02 | 9.00 | |
| C-4 | 133.44 | 8.35 | |
| C-4a | 126.79 | | 9.00 (7.2 Hz) |
| C-5 | 175.98 | | 8.35 (3.5 Hz) |
| C-6 | 135.83 | | 6.88 (3.8 Hz), 3.81 |
| C-7 | 141.60 | | 6.88 |
| C-8 | 180.33 | | 6.88 (6.5 Hz) |
| C-8a | 144.19 | | 8.35 (5.7 Hz) |
| C-2'* | 134.65 | | 2.16 (3.8 Hz) |
| C-3'* | 135.78 | | 2.16 (5.8 Hz) |
| C-4' | 134.12 | | 2.16, 6.61 |
| C-5' | 145.30 | | 7.4 |
| C-6' | 129.69 | | 7.4 (4.0 Hz) |
| | | | 9.00 (1.3 Hz) |
| C-7' | 121.47 | | 8.72, 6.95 |
| C-8' | 143.84 | | 8.72, 7.06, 6.61 |
| C-9' | 148.36 | | 6.95, 3.86, 8.72 |
| C-10' | 112.00 | 7.06 | 6.61 (9.4 Hz) |
| C-11' | 120.24 | 6.95 | 7.06 |
| C-12' | 121.67 | 6.61 | 7.06 (8.0 Hz) |
| OCH3-6 | 59.77 | 3.86 | |
| NH2-7 | | 6.88 | |
| COOH-2' | 167.03 | | 2.16 |
| CH3-3' | 16.93 | 2.16 | |
| NH2-5' | | 7.4 | |
| OCH3-9' | 55.79 | 3.81 | |
| OH-2' | | 12.3 | |
| OH-8' | | 8.72 | |

*May be reversed
$^+$Dimethylsulfoxide

The compounds of the instant invention include 10'-desmethoxystreptonigrin and salts, esters and amides thereof. The term "salts", as used herein, denotes acidic and basic salts, formed with inorganic or organic acids and bases. While pharmaceutically acceptable salts are preferred, particularly when employing the compounds of the invention as medicaments, other salts find utility, for example, in processing these compounds, or where non-medicament-type uses are contemplated.

Particularly preferred are salts with basic substances including, for example, metal salts such as alkali and alkaline earth metal salts, ammonium salts and salts formed with amines such as mono-, di- or trialkylamines (e.g., alkanolamines), diamines (e.g., ethylenediamine and N-substituted ethylenediamine), and hydrazine.

Esters of 10'-desmethoxystreptonigrin are also provided. Exemplary esters may be prepared by esterifying the 2'-position carboxy group of 10'-desmethoxystreptonigrin, for example, by reaction with an organic alcohol, by methods known to the skilled artisan. Organic alcohols employed for esterification may, for example, be those of the formula R—OH where R is aryl or, preferably, alkyl such as methyl, ethyl, propyl or butyl. Also exemplary are esters of 10'-desmethoxystreptonigrin which are hydrolyzable in vivo providing the free acid form.

Amides of 10'-desmethoxystreptonigrin are further provided. Exemplary such compounds are those prepared by forming an amide group at the 2'-position. Preferred are amide compounds where the 2'-position substituent is —C(O)—R$^1$ where R$^1$ is the group —N(R$^2$)(R$^3$) or, if not already covered, an amino acid bonded through the amino group thereof; and R$^2$ and R$^3$ are independently selected from hydrogen, hydroxyl, alkyl, amino, alkylamino, dialkylamino or the group —NHC(X)NH$_2$ where X is oxygen or sulfur. The amides of the instant invention may be prepared by methods known to the skilled artisan.

The term "a salt, ester or amide thereof", when used in reference to 10'-desmethoxystreptonigrin, denotes 10'-desmethoxystreptonigrin in which one or more groups have been modified to a salt, ester or amide group.

The term "alkyl", as used herein, denotes open-chain branched or unbranched groups, or cyclic groups, preferably having 1–12 carbon atoms in the chain or ring system, which may be substituted by appropriate substituents such as one or more hydroxyl, amino, alkylamino, dialkylamino, carboxyl, or alkyloxycarbonyl groups.

The term "aryl", as used herein, preferably denotes phenyl or naphthyl, or phenyl or naphthyl substituted by appropriate substituents such as alkyl or the above substituents recited for alkyl.

It is preferred that the inventive compounds have a degree of purity such that they are suitable for use as an antibiotic and/or antitumor agent. A particularly preferred embodiment of the instant invention provides 10'-desmethoxystreptonigrin, or a salt, ester or amide thereof, in its pure or substantially pure state. The pure or substantially pure compounds are preferably employed in preparing compositions such as those of the instant invention. Further, the pure or substantially pure compounds, alone or as used in compositions exemplified by those described herein, are preferably employed in the methods of the instant invention.

The inventive compounds are useful as antimicrobial agents, useful in inhibiting the growth of, including killing, microorganisms such as bacteria, viruses and protozoa. The inventive compounds are particularly useful as broad-spectrum antibacterial agents, having activity against both gram-positive and gram-negative bacteria, for example, bacteria of the genus Staphylococcus such as *Staphylococcus aureus;* Streptococcus such as *Streptococcus agalactiae* and *Streptococcus faecalis;* Micrococcus such as *Micrococcus luteus;* Bacillus such as *Bacillus subtilis;* Listerella such as *Listerella monocytogenes;* Escherichia such as *Escherichia coli;* Klebsiella such as *Klebsiella pneumoniae;* Proteus such as *Proteus mirabilis* and *Proteus vulgaris;* Salmonella such as *Salmonella typhosa;* Shigella such as *Shigella sonnei;* Enterobacter such as *Enterobacter aerogenes;* Serratia such as *Serratia marcescens;* Pseudomonas such as *Pseudomonas aeruginosa;* Acinetobacter such as *Acinetobacter anitratus;* Nocardia such as *Nocardia autotrophica;* and Mycobacterium such as *Mycobacterium fortuitum.*

Thus, the compounds of the instant invention may be employed in utilities suitable for antimicrobial agents.

The inventive compounds may be, for example, used in treating a host infected with a microorganism, comprising the step of administering to the host 10'-desmethoxystreptonigrin or a physiologically tolerated salt, ester or amide thereof in an amount effective for the treatment. Treatmenty of such infections according to the instant invention includes both mitigation as well as elimination thereof.

Hosts treatable according to the method of the invention include plants and animals, particularly mammals such as dogs, cats and other domestic animals and, especially, humans. The dosage form and mode of administration, as well as the dosage amount, may be selected by the skilled artisan. The dosage amount will vary with the severity of the infection, and with the size and species of the host. Exemplary daily dosages for an adult human are those within the range of from about 100 mg to about 600 mg/day. Administration to a mammalian host may, for example, be oral or parenteral or, especially, topical. Administration to a plant host may be accomplished by, for example, application to seed, foliage or other plant part, or to the soil.

Compositions are also provided by the instant invention which comprise 10'-desmethoxystreptonigrin or a physiologically tolerated salt, ester or amide thereof in a amount effective for the treatment of infection by a microorganism, and a physiologically tolerated vehicle or diluent. The term "physiologically tolerated" is equivalent to the term "pharmaceutically acceptable" when used in reference to the treatment of a mammalian host. The appropriate solid or liquid vehicle or diluent may be selected, and the compositions prepared, by methods known to the skilled artisan. Treatment of simultaneous infections by more than one microorganism is, of course, contemplated.

The inventive compounds may also be employed as antimicrobial agents useful in inhibiting the growth of, including killing, microorganisms present on a surface or in a medium outside a living host. The instant invention therefore provides a method for inhibiting the growth of at least one microorganism present on a surface or in a medium, comprising the step of contacting the surface or medium with 10'-desmethoxystreptonigrin or a salt, ester or amide thereof in an amount effective for the inhibition. Thus, the inventive compounds may be employed, for example, as disinfectants for surface treatments or as preservatives for a variety of solid and liquid media susceptible to microbial growth. Suitable amounts of the inventive compounds may be determined by methods known to the skilled artisan. Compositions comprising 10'-desmethoxystreptonigrin or a salt, ester or amide thereof in an amount effective for inhibiting the growth of at least one microorganism, and a vehicle or diluent, are also provided by the instant invention.

The inventive compounds have further been found to exert an antitumor activity. Thus, the instant invention provides a method for treating a host bearing a tumor, comprising the step of administering to the host 10'-desmethoxystreptonigrin or a physiologically tolerated salt, ester or amide thereof in an amount effective for such treatment. The instant invention includes maintaining or reducing the size, as well as the elimination of, the tumor. The inventive compounds may be used to treat tumors susceptible to such treatment, including human ovarian and colon tumors, as well as those tumors susceptible to the known antitumor agent streptonigrin. Compositions containing the inventive compounds are provided, comprising 10'-desmethoxystreptonigrin or a physiologically tolerated salt, ester or amide thereof in an amount effective for the treatment of a tumor, and a physiologically tolerated vehicle or diluent.

Hosts, dosages, modes of administration, etc., described above for the treatment of a host infected with a microorganism, apply to the use of the instant compounds as antitumor agents, and those descriptions are incorporated herein.

10'-Desmethoxystreptonigrin has been found to inhibit the farnesylation of ras oncogene p21 protein, and thus may be expected to block the neoplastic effect of ras oncogenes in tumor cells. The instant invention also therefore provides a method for preventing the formation of a tumor in a host, comprising the step of administering to the host 10'-desmethoxystreptonigrin or a physiologically tolerated salt, ester or amide thereof in an amount effective for such prevention. Compositions containing the inventive compounds are provided, comprising 10'-desmethoxystreptonigrin or a physiologically tolerated salt, ester or amide thereof in an amount effective to prevent a tumor, and a physiologically tolerated vehicle or diluent.

Hosts, tumors, dosages, modes of administration, etc., described above for the treatment of a host bearing a tumor, apply to the use of the instant compounds as tumor preventatives, and those descriptions are incorporated herein.

The following examples further illustrate the invention, and are not intended to in any way limit the instant claims.

EXAMPLE 1

Preparation of 10'-Desmethoxystreptonigrin

This example demonstrates an exemplary method for the preparation of 10'-desmethoxystreptonigrin by cultivation of a strain of *Streptomyces albus*.

Tomato paste-oatmeal agar slants were seeded with *Streptomyces albus* A.T.C.C. No. 55161 and incubated at 25° C. for 72 hours. The growth was used to inoculate 50 ml portions of an aqueous medium contained in 250 mL Erlenmeyer flasks. The composition of the germination medium was:

| | |
|---|---|
| Yeast extract | 4.0 g |
| Malt extract | 10.0 g |
| Dextrose | 4.0 g |
| Distilled water | 1000 mL |

The medium, adjusted to pH 7.3, was sterilized at 121° C. for 20 minutes prior to use.

The inoculated germination flasks were incubated at 25° C. on a rotary shaker for about 72 hours. The shaker operated at a speed of 300 rpm with a 2-inch stroke. At that time, a 5% transfer was made from the growth in the germination flasks to 50 mL portions of fermentation medium contained in 250 mL Erlenmeyer flasks. The composition of the fermentation medium was:

| | |
|---|---|
| Pharmamedia* | 20 g |
| Glucose | 50 g |
| CaCO$_3$ | 7 g |
| Distilled water | 1000 mL |

*A commercially available protein source derived from cottonseed meal.

The medium was sterilized at 121° C. for 30 minutes prior to use.

The inoculated flasks were incubated for about 120 hours at 25° C. on a rotary shaker operating at 300 rpm with a 2-inch stroke.

At harvest, the pooled contents of 200 flasks were centrifuged to separate the mycelium from the broth supernatant. About 8 liters of broth supernatant were so obtained. The pH of the broth supernatant was adjusted to about 3 by the addition of 1N HCl, after which the acidified broth was extracted twice with ethyl acetate, first with 4 liters and then with 2 liters. The organic extracts were combined and the pool was then extracted with 2 successive portions of 5% aqueous sodium carbonate, first with 3 liters and then with 1 liter. The aqueous layers were pooled and the resulting 4 liters were slowly adjusted to a pH of about 3 by the addition of concentrated HCl. Caution was exercised during the acidification step to prevent excessive and rapid foaming. The acidified solution was then extracted twice with 2 liter portions of ethyl acetate. The ethyl acetate extracts were pooled and the pool was concentrated to dryness in vacuo, to give 5.3 g of residue. This residue was dissolved in approximately 20 ml of methanol, with gentle warming. The methanol solution was charged onto a DEAE cellulose column, 5.0×15 cm, packed in methanol, and column was washed liberally with methanol to remove inactive impurities. The column was then developed with a solvent mixture consisting of 1% acetic acid in methanol, with a flow rate of 1 ml per minute. 10 mL fractions were collected and analyzed for activity against *Staphylococcus aureus* 209P. The active fractions were combined and concentrated to dryness, resulting in crystals. These were recrystallized from acetone, giving 50 mg of pure, crystalline 10'-desmethoxystreptonigrin as blackish-red needles.

EXAMPLE 2

Biological Activities (A) Determination of MIC against bacteria

The following methodology was used to determine the minimum inhibitory concentration (hereinafter referred to as MIC) of 10'-desmethoxystreptonigrin against bacteria. The test organisms were grown in 20 ml of Antiobiotic Assay Broth (Difco) by inoculating the broth (in tubes) with a loopful of the organism from a BHI (Difco) agar slant. The inoculated tubes were incubated at 37° C. for 18 to 24 hours. These cultures were assumed to contain $10^9$ colony forming units (CFU) per ml. The cultures were diluted 1:100 to give a final inoculum level of $10^7$ CFU; dilutions were made with Yeast-Beef Broth (Difco). The test compound was dissolved in an appropriate diluent at a concentration of 1,000 μg/ml. Two-fold dilutions were made in Yeast-Beef Broth (Difco), resulting in a range from 1000 μg/ml to 0.5 μg/ml. A 1.5 ml portion of each dilution was placed into individual petri dishes to which 13.5 ml of K-10 agar was added. The composition of K-10 agar is:

| | |
|---|---|
| Beef extract | 1.5 g |
| Yeast extract | 3.0 g |
| Peptone | 6.0 g |
| Dextrose | 1.0 g |
| Agar | 15.0 g |
| Distilled water | q.s. to 1000 ml |

The medium was sterilized at 121° C. for 15 minutes at 15 lbs. psi.

The final drug concentration in the agar ranged from 100 μg/mL to 0.05 μg/mL. Organism growth control plates containing agar only were prepared and inoculated before and after the test plates. The organisms were applied to the agar surface of each plate with a Denly Multipoint Inoculator (which delivers approximately 0.001 mL of each inoculum) resulting in a final inoculum of $10^4$ CFU on the agar plate.

The plates were incubated at 37° C. for 18 hours and the MICs determined. The MIC is the lowest concentration of compound inhibiting growth of the organism.

The results of the agar dilution assays with bacteria are shown in Table 1. These results demonstrate the broad-spectrum activity of 10'-desmethoxystreptonigrin against both gram-positive and gram-negative bacteria.

TABLE 1

Antibacterial Activity in Vitro of 10'-Desmethoxystreptonigrin

| Organism | Strain Designation (SC#)* | Minimum Inhibitory Concentration (MIC) (μg/mL) |
|---|---|---|
| Staphylococcus aureus | 1276 | 0.4 |
| Staphylococcus aureus | 2399 | 0.2 |
| Staphylococcus aureus | 2400 | 0.2 |
| Staphylococcus aureus | 10165 | 0.2 |
| Streptococcus faecalis | 9011 | 1.6 |
| Streptococcus faecalis | 9610 | 1.6 |
| Streptococcus agalactiae | 9287 | 1.6 |
| Streptococcus agalactiae | 14008 | 1.6 |
| Micrococcus luteus | 2495 | 0.4 |
| Bacillus subtilis | 3777 | 0.2 |
| Listerella monocytogenes | 8523 | 1.6 |
| Escherichia coli | 8294 | 3.1 |
| Escherichia coli | 10857 | 0.8 |
| Escherichia coli | 10896 | 0.4 |
| Escherichia coli | 10909 | <0.05 |
| Escherichia coli | 12864 | 1.6 |
| Klebsiella pneumoniae | 10440 | 3.1 |
| Klebsiella pneumoniae | 9527 | 3.1 |
| Proteus mirabilis | 3855 | 3.1 |
| Proteus vulgaris | 9416 | 0.4 |
| Salmonella typhosa | 1195 | 1.6 |
| Shigella sonnei | 8449 | 1.6 |
| Enterobacter cloacae | 8236 | >100 |
| Enterobacter aerogenes | 10078 | 25 |
| Serratia marcescens | 9783 | 6.3 |
| Pseudomonas aeruginosa | 9545 | 1.6 |
| Pseudomonas aeruqinosa | 8329 | 6.3 |
| Pseudomonas cepacia | 14164 | >25 |
| Acinetobacter calcoaceticus | 8333 | >100 |
| Acinetobacter anitratus | 14207 | 3.1 |
| Nocardia autotrophica | 8994 | 3.1 |
| Mycobacterium fortuitum | 8571 | 50 |

*"SC#" denotes the number used by Bristol-Myers Squibb Company in identifying the strain.

(b) In vitro cytotoxicity vs. human tumor cell lines

10'-Desmethoxystreptonigrin was also tested for cytotoxicity in vitro against human tumor cell lines according to the method of Catino et al., "A microtitre cytotoxicity assay useful for the discovery of fermentation derived antitumor agents", Cancer Chemother., Pharmacol. 15: 240-243 (1985). Modification of the dye employed therein was made according to Scudiero et al., "Evaluation of a soluble tetrazolium/formazan assay for cell growth and drug sensitivity in culture using human and other tumor cell lines," Cancer Research 48:4827-4833,1 (1988). The assays were performed in triplicate against human ovarian (A2780DDP and A2780S) and colon (HCT-116, HCT/VM46 and HCT/VP35) tumor cell lines. Such cell lines are, for example, described by Long et al., "The effects of mitomycin on human colon carcinoma cells," J. Nat. Cancer Inst. 73: 787–792 (1984) (HCT-116) and Masuda et al., "Increased DNA repair as a mechanism of acquired resistance to cis-diamminedichloroplatinum (II) in human ovarian cancer cell lines," Cancer Research 48: 5713–5716 (1988) (A2780).

The results of these assays, shown in Table 2, demonstrate the utility of 10'-desmethoxystreptonigrin against human tumor cell lines.

TABLE 2

Cytotoxicity Activity in vitro of 10'-Desmethoxystreptonigrin

| Compound 10'-desmethoxy-streptonigrin | IC$_{50}$ (μg/ml) Human Tumor Cell Lines*+ | | | | |
|---|---|---|---|---|---|
| | A2780DDP | A2780S | HCT-116 | HCT/VM46 | HCT/VP35 |
| | 0.010 | 0.001 | 0.006 | 0.001 | 0.003 |
| | 0.002 | 0.002 | 0.003 | 0.002 | 0.002 |
| | 0.008 | <0.001 | 0.003 | <0.001 | 0.003 |

*A2780DDP Human ovarian cells, resistant to diamminedichloroplatinum
A2780S Human ovarian cells
HCT-116 Human colon cells
HCT/VM46 Human colon cells, resistant to the antitumor agent, teniposide (4'-demethylepipodophyllotoxin thenylidiene-β-D-glucoside)
HCT/VP35 Human colon cells, resistant to the antitumor agent, etoposide (demethylepipodophyllotoxin ethylidene-β-D-glucoside)
+In vivo tests in mice using the intraperitoneally implanted P388 murine leukemia model provided no statistically significant increase in lifespan compared to control groups at nontoxic levels of 10'-desmethoxystreptonigrin.

(c) Inhibition of farnesylation of p21 ras protein

Employing the assay described by Manne et al., "Identification and preliminary characterization of protein-cysteine farnesyltransferase", Proc. Natl. Acad. Sci. USA 87: 7541–7545 (1990), 10'-desmethoxystreptonigrin was found to have an IC$_{50}$ value of $2.35 \times 10^{-5}$M in inhibiting the farnesylation of p21 ras protein.

What is claimed is:

1. The strain of *Streptomyces albus* designated by A.T.C.C. No. 55161 which is biologically pure.

2. A strain of *Streptomyces albus* which has all of the identifying characteristics of the strain designated by A.T.C.C. No. 55161, which is biologically pure, and which is capable of producing the compound 5'-amino-6'-(7-amino-5,8-dihydro-6-methoxy-5,8-dioxo-2-quinolyl)-4'-(8'-hydroxy-9'-methoxyphenyl)-3'-methyl-2'-pyridinecarboxylic acid.

3. A method for the preparation of the compound 5'-amino-6'-(7-amino-5,8-dihydro-6-methoxy-5,8-dioxo-2-quinolyl)-4'-(8'-hydroxy-9'methoxyphenyl)-3'-methyl-2'-pyridinecarboxylic acid, or a salt, ester or amide thereof, comprising the step of fermenting the microorganism of claim 1, and isolating said compound.

4. A method for the preparation of the compound 5'amino-6'-(7-amino-5,8-dihydro-6-methoxy-5,8-dioxo-2-quinolyl)-4'-(8'-hydroxy-9'-methoxyphenyl)3'-methyl-2'-pyridinecarboxylic acid, or a salt, ester or amide thereof, comprising the step of fermenting the microorganism of claim 2 and isolating said compound.

* * * * *